United States Patent
Onishi et al.

(10) Patent No.: US 10,499,800 B2
(45) Date of Patent: *Dec. 10, 2019

(54) ENDOSCOPE REPROCESSSOR

(71) Applicants: OLYMPUS CORPORATION, Tokyo (JP); HORIBA Advanced Techno, Co., Ltd., Kyoto-shi, Kyoto OT (JP)

(72) Inventors: Hideto Onishi, Hachioji (JP); Hiromasa Akahori, Tachikawa (JP); Yumiko Awau, Tokyo (JP); Akihisa Ogawa, Hachioji (JP); Shintaro Suzuki, Sagamihara (JP); Yoshihiko Kawaguchi, Kyoto (JP); Satoko Kai, Kyoto (JP)

(73) Assignees: OLYMPUS CORPORATION, Tokyo (JP); HORIBA Advanced Techno, Co., Ltd., Kyoto-shi, Kyoto (JP)

( * ) Notice: Subject to any disclaimer, the term of this patent is extended or adjusted under 35 U.S.C. 154(b) by 111 days.

This patent is subject to a terminal disclaimer.

(21) Appl. No.: 15/807,637

(22) Filed: Nov. 9, 2017

(65) Prior Publication Data
US 2018/0064324 A1    Mar. 8, 2018

Related U.S. Application Data

(63) Continuation of application No. PCT/JP2016/063743, filed on May 9, 2016.

(30) Foreign Application Priority Data

May 21, 2015    (JP) .................................. 2015-103883

(51) Int. Cl.
*A61B 1/12*    (2006.01)
*A61L 2/18*    (2006.01)
(Continued)

(52) U.S. Cl.
CPC .......... *A61B 1/121* (2013.01); *A61B 1/00057* (2013.01); *A61B 1/123* (2013.01);
(Continued)

(58) Field of Classification Search
CPC combination set(s) only.
See application file for complete search history.

(56) References Cited

U.S. PATENT DOCUMENTS

2003/0209450 A1    11/2003    McVey et al.
2011/0308946 A1    12/2011    Wilke

FOREIGN PATENT DOCUMENTS

CN    102265146 A    11/2011
EP    3 289 962 A1    3/2018
(Continued)

OTHER PUBLICATIONS

International Search Report dated Jul. 19, 2016 issued in PCT/JP2016/063743.
(Continued)

*Primary Examiner* — Jason Y Ko
(74) *Attorney, Agent, or Firm* — Scully, Scott, Murphy & Presser P.C.

(57) ABSTRACT

An endoscope reprocessor includes a concentration sensor including a concave section in which a sensing section is housed and a permeable membrane configured to cover the concave section, a medicinal solution tank, to an inside of which at least the permeable membrane is exposed and on the inside of which a disinfection solution is stored, and a heating section configured to heat at least the permeable membrane.

7 Claims, 8 Drawing Sheets

(51) Int. Cl.
*B08B 9/023* (2006.01)
*B08B 9/032* (2006.01)
*A61B 1/00* (2006.01)

(52) U.S. Cl.
CPC .............. *A61B 1/125* (2013.01); *A61B 1/128* (2013.01); *A61L 2/18* (2013.01); *B08B 9/023* (2013.01); *B08B 9/0325* (2013.01); *A61L 2202/14* (2013.01); *A61L 2202/17* (2013.01); *A61L 2202/24* (2013.01)

(56) References Cited

FOREIGN PATENT DOCUMENTS

| | | |
|---|---|---|
| JP | S60-074043 U | 5/1985 |
| JP | H03-082437 A | 4/1991 |
| JP | H06-043132 A | 2/1994 |
| JP | 2010-057792 A | 3/2010 |
| JP | 2010-119592 A | 6/2010 |
| JP | 2013-064702 A | 4/2013 |

OTHER PUBLICATIONS

Extended Supplementary European Search Report dated Dec. 6, 2018 in European Patent Application No. 16 79 6323.0.
Jie, L. et al., "Effect of Temperature on Performance of Forward Osmosis Process", Chinese Journal of Environmental Engineering, Oct. 2014, vol. 8, No. 10, pp. 4168-4174.

ENDOSCOPE REPROCESSSOR

CROSS REFERENCE TO RELATED APPLICATION

This application is a continuation application of PCT/JP2016/063743 filed on May 9, 2016 and claims benefit of Japanese Application No. 2015-103883 filed in Japan on May 21, 2015, the entire contents of which are incorporated herein by this reference.

BACKGROUND OF THE INVENTION

1. Field of the Invention

The present invention relates to an endoscope reprocessor including a concentration sensor including a concave section in which a sensing section is housed and a permeable membrane configured to cover the concave section in a medicinal solution tank.

2. Description of the Related Art

Medicinal solution treatment of an endoscope in which the endoscope reprocessor is used is performed by supplying a medicinal solution stored in a medicinal solution tank to a cleaning and disinfecting tub and immersing the endoscope in the medicinal solution at a service temperature for a predetermined time in the cleaning and disinfecting tub.

In order to surely perform the medicinal solution treatment of the endoscope, concentration control of medically effective components of the medicinal solution is important to prevent a medical effect from being deteriorated.

This is because, in the medicinal solution, concentration of some medically effective components in the medicinal solution decreases from initial concentration because of repeated use and natural deterioration. Note that, in the following explanation, concentration of a medically effective component in a medicinal solution is referred to as medicinal solution concentration.

Therefore, in general, a check of the medicinal solution concentration is periodically performed in each medicinal solution treatment process of the endoscope.

Japanese Patent Application Laid-Open Publication No. 2010-57792 discloses an endoscope cleaning and disinfecting apparatus in which a concentration sensor for a medicinal solution is provided in a medicinal solution tank.

More specifically, Japanese Patent Application Laid-Open Publication No. 2010-57792 discloses the endoscope cleaning and disinfecting apparatus that can automatically confirm whether medicinal solution concentration is equal to or higher than effective concentration without separately sampling a medicinal solution because an electrode is provided that is in contact with the medicinal solution and applies a constant voltage to cause an electrochemical reaction with the medicinal solution and measure the medicinal solution concentration.

Therefore, a configuration of a concentration sensor is also well-known in which, for example, in a medicinal solution tank, an electrode is provided in a concave section and the concave section is covered by a permeable membrane having porosities through which liquid does not permeate and only gas permeates, whereby organic matter and the like in the medicinal solution is prevented from adhering to the electrode by the permeable membrane.

In such a configuration of the concentration sensor in which the permeable membrane is used, an internal solution different from the medicinal solution is sealed by the permeable membrane and is in contact with the permeable membrane in the concave section.

Therefore, when the permeable membrane is in contact with the medicinal solution, using a difference in component concentration between the medicinal solution and the internal solution, a medically effective component of the medicinal solution permeates through the permeable membrane making use of an osmotic pressure following evaporation and mixes with the internal solution.

As a result, the electrode can measure medicinal solution concentration via the internal solution.

Figure 14:
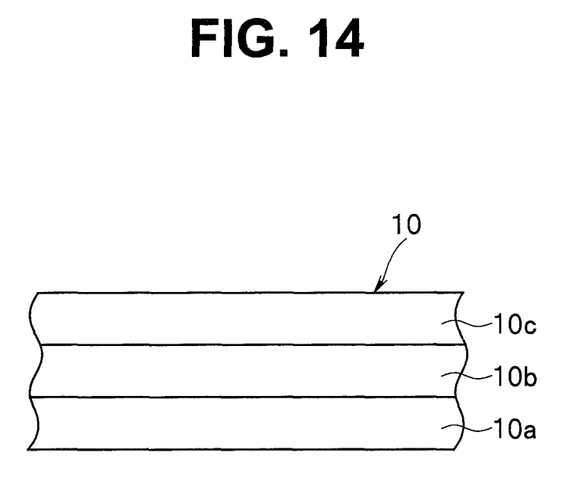
FIG. 14 is a diagram schematically showing a state in which an internal solution and a medicinal solution permeate into a permeable membrane in a concentration sensor.
Figure 15:
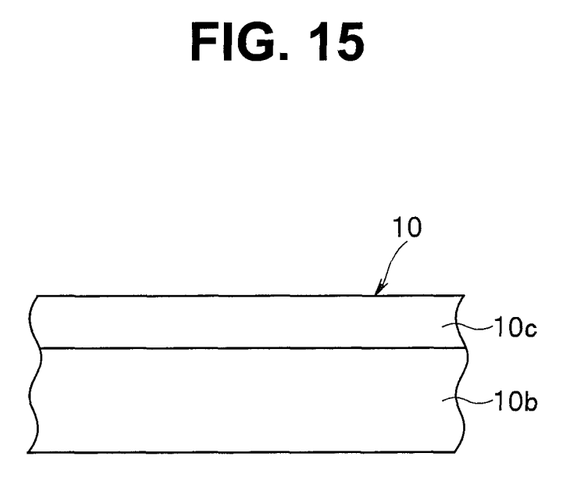
FIG. 15 is a diagram schematically showing a state in which only the internal solution permeates into the permeable membrane in the concentration sensor.

FIG. 14 is a diagram schematically showing a state in which the internal solution and the medicinal solution permeate into the permeable membrane in the concentration sensor. FIG. 15 is a diagram schematically showing a state in which only the internal solution permeates into the permeable membrane in the concentration sensor.

When the medicinal solution is filled in the medicinal solution tank and a permeable membrane 10 is in contact with the medicinal solution, as shown in FIG. 14, the permeable membrane 10 has a three-layer structure in which a region 10a into which the medicinal solution permeates is formed on one surface side of the permeable membrane 10, a region 10c into which the internal solution permeates is formed on the other surface side of the permeable membrane 10, and a region 10b in which the permeable membrane 10 is dry is formed substantially in a center between the one surface and the other surface.

Therefore, the medically effective component in the medicinal solution evaporates from the region 10a, permeates through porosities of the region 10b, thereafter permeates into the region 10c, and thereafter mixes with the internal solution.

However, if the medicinal solution is let out from the medicinal solution tank and left untouched after, for example, replacement of the medicinal solution in the medicinal solution tank, as shown in FIG. 15, the permeable membrane 10 changes to a two-layer structure of the region 10c into which the internal solution permeates and the dry region 10b including a size of the region 10a shown in FIG. 14.

SUMMARY OF THE INVENTION

An endoscope reprocessor according to an aspect of the present invention includes: a concentration sensor including a concave section in which a sensing section is housed and a permeable membrane configured to cover the concave section; a medicinal solution tank, at least the permeable membrane being exposed to an inside of the medicinal solution tank and a medicinal solution being stored in the inside of the medicinal solution tank; and a heating section configured to heat at least the permeable membrane.

DETAILED DESCRIPTION OF THE PREFERRED EMBODIMENT(S)

Embodiments of the present invention are explained below with reference to the drawings. Note that the figures are schematic and relations between thicknesses and widths of respective members, ratios of the thicknesses of the respective members, and the like are different from real ones. It goes without saying that portions, relations and ratios of dimensions thereof that are different, are included among the drawings. Note that, in the embodiments explained below, as an endoscope reprocessor, an endoscope cleaning and disinfecting apparatus is explained as an example. As concentration of a medicinal solution measured with a concentration sensor included in the endoscope cleaning and disinfecting apparatus, concentration of a disinfection solution, more specifically, concentration of peracetic acid in the disinfection solution is explained as an example.

First Embodiment

Figure 1:
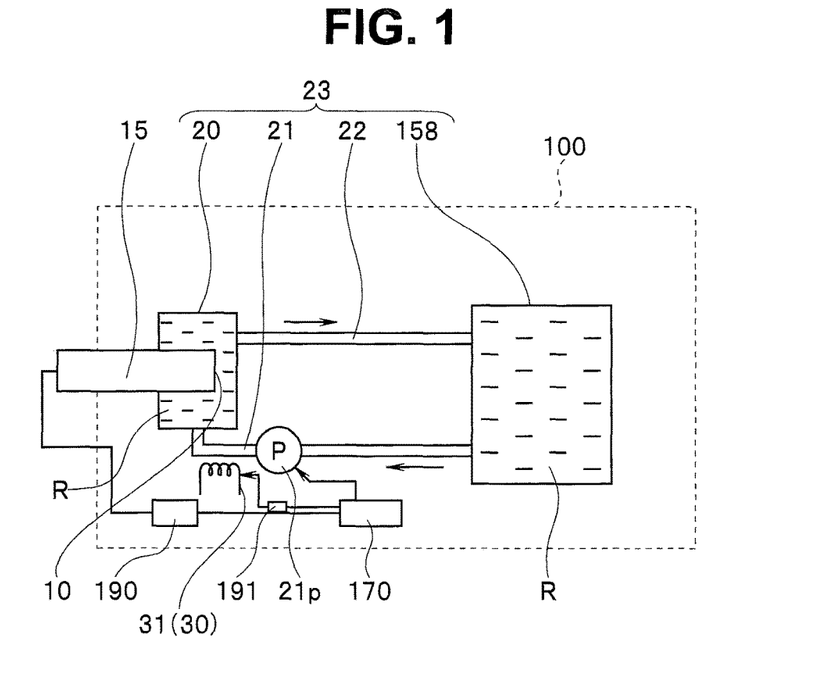
FIG. 1 is a diagram schematically showing a configuration of an endoscope cleaning and disinfecting apparatus of a first embodiment.
Figure 2:
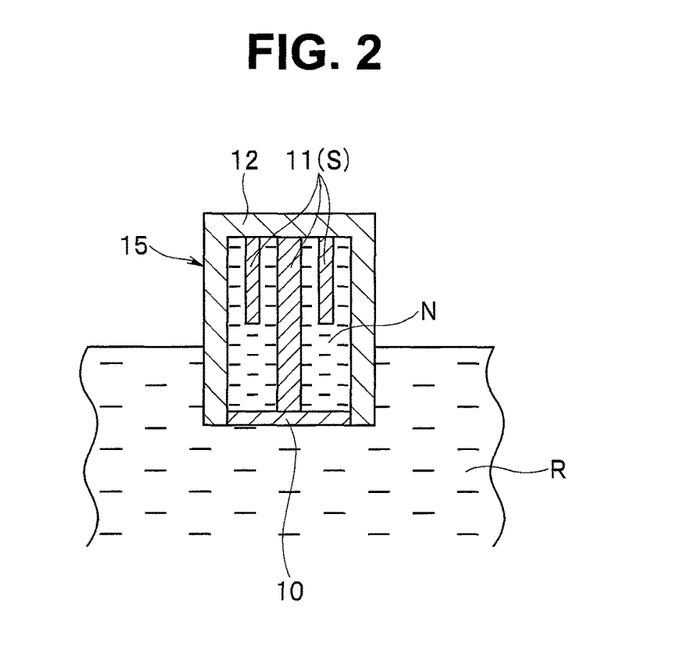
FIG. 2 is a partial sectional view showing, together with a disinfection solution, a configuration of a concentration sensor of the endoscope cleaning and disinfecting apparatus shown in FIG. 1.

FIG. 1 is a diagram schematically showing a configuration of an endoscope cleaning and disinfecting apparatus of a first embodiment. FIG. 2 is a partial sectional view showing, together with a disinfection solution, a configuration of a concentration sensor of the endoscope cleaning and disinfecting apparatus shown in FIG. 1.

As shown in FIG. 1, an endoscope cleaning and disinfecting apparatus 100 includes a concentration sensor 15, a medicinal solution tank 23, a heating section 30, a control section 170, a concentration measuring section 190, and a temperature control section 191.

A main part of the medicinal solution tank 23 is configured by including a main body section 158 in which a disinfection solution R is stored, the main body section 158 supplying the disinfection solution R to a cleaning and disinfecting tub 104 explained below (see FIG. 13), a concentration measurement chamber 20 having a capacity smaller than a capacity of the main body section 158, the concentration sensor 15 being disposed on an inside of the concentration measurement chamber 20, a medicinal-solution lead-in section 21 configured to introduce the disinfection solution R into the concentration measurement chamber 20 from the main body section 158, and a medicinal-solution lead-out section 22 configured to introduce the disinfection solution R into the main body section 158 from the concentration measurement chamber 20.

The concentration sensor 15 includes, as shown in FIG. 2, a concave section 12 in which a sensing section S is housed and a permeable membrane 10 configured to cover the concave section 12. In the present embodiment, the concentration sensor 15 is disposed such that at least the permeable membrane 10 is exposed on the inside of the concentration measurement chamber 20.

As explained above, the permeable membrane 10 is configured of a material having porosities through which liquid does not permeate and only gas permeates. Note that examples of the material configuring the permeable membrane 10 include silicone.

An inside of the concave section 12 may be a hollow section. However, when an electrode 11 configured to measure concentration of a detection target is used as the sensing section S, it is desirable that an internal solution N different from the disinfection solution R is sealed in the concave section 12 by the permeable membrane 10.

A composition of the internal solution is not particularly limited and can be determined as appropriate according to a detection target. For example, when peracetic acid concentration in a peracetic acid mixed solution is detected, as the internal solution, for example, a phosphate buffer solution, an acetic acid buffer solution, tris hydroxymethyl aminomethane, a boric acid buffer solution, or a citrate buffer solution can be used.

Using a difference in component concentration between the disinfection solution R and the internal solution N, peracetic acid in the disinfection solution R permeates through the permeable membrane 10 making use of an osmotic pressure following evaporation and mixes in the internal solution N, whereby the concentration measuring section 190 measures, according to driving control by the control section 170, peracetic acid concentration via the internal solution N using an electrochemical reaction between the electrode 11, to which a constant voltage is applied from the concentration measuring section 190, and the internal solution N.

Note that, on one hand, in a state in which the disinfection solution R is led into the concentration measurement chamber 20 and is in contact with the disinfection solution R as shown in FIG. 2, the permeable membrane 10 has the three-layer structure including the regions 10a, 10b, and 10c as shown in FIG. 14 referred to above. On the other hand, when the disinfection solution R is not led into the concentration measurement chamber 20, as shown in FIG. 15 referred to above, the permeable membrane 10 is dry and has the two-layer structure including only the regions 10b and 10c.

Referring back to FIG. 1, the medicinal-solution lead-in section 21 is a conduit configured to connect the main body section 158 and the concentration measurement chamber 20 and introduce the disinfection solution R in the main body section 158 into the concentration measurement chamber 20.

More specifically, a medicinal-solution transfer section 21p configured to transfer the disinfection solution R in the main body section 158 is provided in a halfway position of the medicinal-solution lead-in section 21. The disinfection solution R in the main body section 158 is supplied into the concentration measurement chamber 20 according to driving of the medicinal-solution transfer section 21p involved in the driving control by the control section 170. Note that the medicinal-solution transfer section 21p is configured of, for example, a pump.

The medicinal-solution lead-out section 22 is a conduit configured to connect the concentration measurement chamber 20 and the main body section 158 and return the disinfection solution R in the concentration measurement chamber 20 into the main body section 158.

Therefore, when the medicinal-solution transfer section 21p is driven, the disinfection solution R circulates between the main body section 158 and the concentration measurement chamber 20 via the medicinal-solution lead-in section 21 and the medicinal-solution lead-out section 22.

When the peracetic acid permeates through the permeable membrane 10 and mixes with the internal solution N, the peracetic acid included in the disinfection solution R near the permeable membrane 10 decreases. Therefore, it is desirable that the disinfection solution R continues to circulate during measurement of concentration such that a new disinfection solution R can always be led into the concentration measurement chamber 20.

The heating section 30 is electrically connected to the temperature control section 191. The heating section 30 heats at least the disinfection solution R near the permeable membrane 10 according to the driving control by the control section 170 performed via the temperature control section 191. Note that the heating section 30 is configured of, for example, a heater 31.

More specifically, in the present embodiment, the heater 31 is provided in a halfway position of the medicinal-solution lead-in section 21. The heater 31 heats the medicinal-solution lead-in section 21 and heats the disinfection solution R that passes the medicinal-solution lead-in section 21. Note that the heater 31 may be provided in the concentration measurement chamber 20.

The heater 31 heats the disinfection solution R to a temperature higher than an actual service temperature of the disinfection solution R. More specifically, for example, when the disinfection solution R is heated to 20° C. in disinfection of the endoscope, the heater 31 desirably heats the disinfection solution R to a temperature exceeding 20° C.

When the disinfection solution R is heated, since an evaporation amount of the peracetic acid in the disinfection solution R increases, the peracetic acid permeates into the permeable membrane 10 more quickly than usual.

The service temperature referred to herein is different depending on a composition of the medicinal solution R. For example, when Acecide (registered trademark) having peracetic acid concentration of 0.2% is used as the medicinal solution R, the service temperature is desirably 20° C. to 25° C.

Since the heater 31 is provided in the concentration measurement chamber 20, there is an advantage that thermal deterioration by the heater 31 is prevented from affecting the disinfection solution in the main body section 158.

Therefore, in the present embodiment, the concentration measurement chamber 20 having the capacity smaller than the capacity of the main body section 158 is provided separately from the main body section 158. The concentration sensor 15 is provided in the concentration measurement chamber 20. Further, only a small amount of the disinfection solution R supplied into the concentration measurement chamber 20 is heated by the heater 31, whereby quick permeation of the disinfection solution R into the permeable membrane 10 in the concentration measurement chamber 20 is promoted and the deterioration of the disinfection solution R is minimized.

Note that, in order to prevent the deterioration of the disinfection solution R used for the disinfection of the endoscope, the disinfection solution R used for concentration detection by the concentration sensor 15 may be discarded without being returned to the main body section 158 via the medicinal-solution lead-out section 22 or may be cooled by a known Peltier element, heat sink, or the like provided in the medicinal-solution lead-out section 22 and returned to the main body section 158.

In this way, in the present embodiment, the concentration sensor 15 is provided in the concentration measurement chamber 20. The heating section 30 configured to heat the permeable membrane 10 of the concentration sensor 15 by heating the disinfection solution R is provided in the concentration measurement chamber 20 or the medicinal-solution lead-in section 21.

Consequently, even if the permeable membrane 10 is dried and configured of the two layers of the regions 10b and 10c and the dried region 10b is formed larger than the region 10b shown in FIG. 14 as shown in FIG. 15 referred to above, it is possible to cause the disinfection solution R to quickly permeate into the permeable membrane 10 by heating, with the heating section 30, the disinfection solution R supplied into the concentration measurement chamber 20. Therefore, it is possible to further improve permeation speed of the evaporated peracetic acid in the disinfection solution R through the permeable membrane 10 than in the past.

Therefore, even after the disinfection solution R is injected into the main body section 158, it is possible to accurately perform the concentration measurement of the disinfection solution R.

The concentration measurement of the disinfection solution R performed using the concentration sensor 15 can be performed in the concentration measurement chamber 20 different from the main body section 158. Therefore, in the endoscope cleaning and disinfecting apparatus 100, the concentration measurement chamber 20 can be disposed in a free position. Therefore, for example, if the concentration measurement chamber 20 is disposed in an upper part of the endoscope cleaning and disinfecting apparatus 100, it is easy to perform replacement work of the concentration sensor 15. Moreover, as explained above, it is possible to minimize the deterioration of the disinfection solution R involved in the heating.

Therefore, it is possible to provide the endoscope cleaning and disinfecting apparatus 100 including a configuration that can cause the disinfection solution R to quickly permeate into the dried permeable membrane 10 and can accurately measure medicinal solution concentration.

Figure 3:
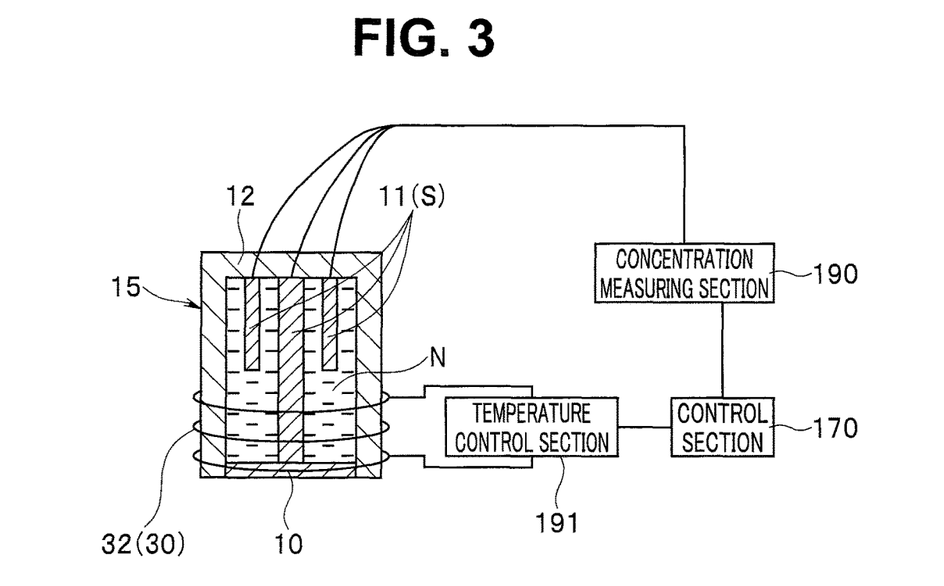
FIG. 3 is a partial sectional view showing, together with a control section, a concentration measuring section, and a temperature control section, a modification in which a heating section shown in FIG. 1 is provided in a concentration sensor.
Figure 4:
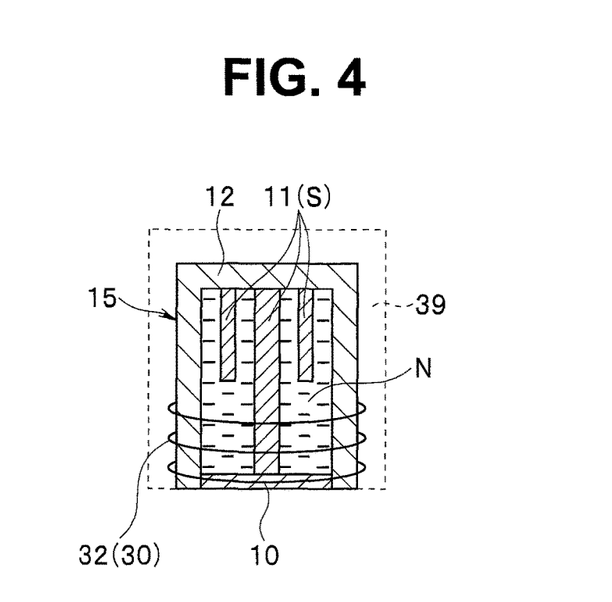
FIG. 4 is a partial sectional view showing a configuration in which a heat insulating material is provided to cover an outer circumference of a concave section of the concentration sensor shown in FIG. 3.
Figure 5:
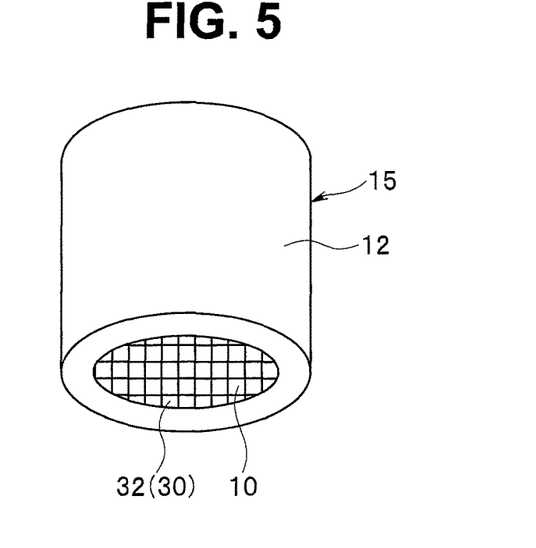
FIG. 5 is a perspective view showing a modification in which the heating section is provided in a permeable membrane shown in FIG. 2.

Note that modifications are explained below with reference to FIG. 3 to FIG. 5. FIG. 3 is a partial sectional view showing, together with the control section, the concentration measuring section, and the temperature control section, a modification in which the heating section shown in FIG. 1 is provided in a concentration sensor. FIG. 4 is a partial sectional view showing a configuration in which a heat insulating material is provided to cover an outer circumference of the concave section of the concentration sensor shown in FIG. 3. FIG. 5 is a perspective view showing a modification in which the heating section is provided in the permeable membrane shown in FIG. 2.

In the present embodiment explained above, the heating section 30 is configured of the heater 31 and provided in the concentration measurement chamber 20 or the medicinal-solution lead-in section 21. The heating section 30 heats the disinfection solution R to thereby heat the permeable membrane 10.

Independently of this, in order to prevent the deterioration of the disinfection solution R involved in the heating of the disinfection solution R, as shown in FIG. 2, the permeable membrane 10 may be directly heated in a state in which the permeable membrane 10 is immersed in the disinfection solution R.

More specifically, as shown in FIG. 3, the heating section 30 may be configured of a heater including an electric heating wire 32 wound around to be in contact with at least the permeable membrane 10 as well on an outer circumference of the concave section 12.

Note that, like the heater 31, the electric heating wire 32 is also electrically connected to the temperature control section 191. The temperature control section 191 is controlled to be driven by the control section 170, whereby the electric heating wire 32 directly heats at least the permeable membrane 10.

Note that, as shown in FIG. 4, a heat insulating material 39 may be provided to cover the concave section 12. The heat insulating material 39 has a function of preventing heat given to the permeable membrane 10 by the electric heating wire 32 from escaping. If the heat insulating material 39 is used, it is possible to efficiently heat the permeable membrane 10 by the electric heating wire 32.

As shown in FIG. 5, the electric heating wire 32 may be provided, for example, in a lattice shape in the permeable membrane 10. Consequently, it is also possible to efficiently heat the permeable membrane 10 by the electric heating wire 32.

A configuration of the heating section 30 configured to directly heat the permeable membrane 10 other than the electric heating wire 32 is explained below with reference to FIG. 6 and FIG. 7.

Figure 6:
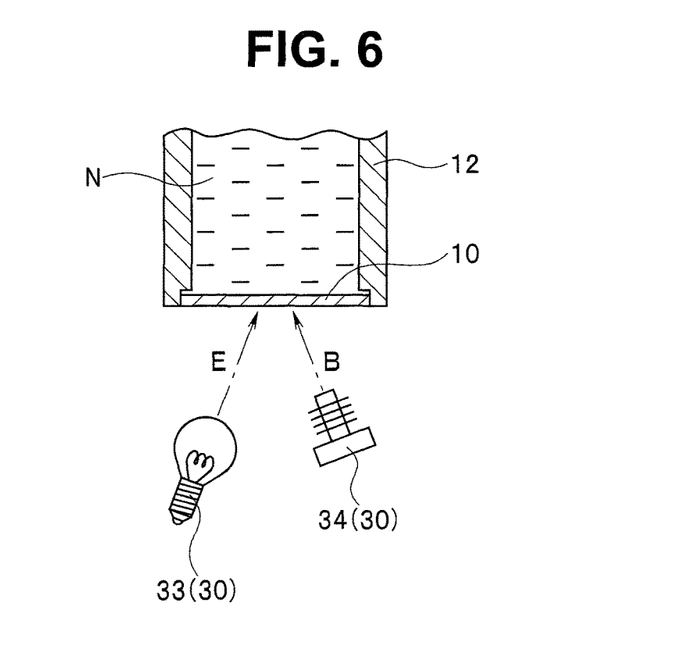
FIG. 6 is a partial sectional view showing, together with a part of the concentration sensor, a modification in which the heating section shown in FIG. 1 is configured of a far infrared ray lamp or an electron beam irradiator.

FIG. 6 is a partial sectional view showing, together with a part of the concentration sensor, a modification in which the heating section shown in FIG. 1 is configured of a far infrared ray lamp or an electron beam irradiator. FIG. 7 is a partial sectional view showing, together with a part of the concentration sensor, a state in which an electron beam irradiated from the electron beam irradiator shown in FIG. 6 is intensively irradiated on the permeable membrane by a reflection member.

As shown in FIG. 6, the heating section 30 may be configured of a far infrared ray lamp 33 configured to irradiate a far infrared ray E on the permeable membrane 10 and directly heat the permeable membrane 10 and an electron beam irradiator 34 configured to irradiate an electron beam B on the permeable membrane 10 and directly heat the permeable membrane 10.

In the configuration shown in FIG. 6, it is likely that components other than the permeable membrane 10 are also heated. However, as shown in FIG. 7, if the electron beam B irradiated from the electron beam irradiator 34 is intensively irradiated on the permeable membrane 10 using a reflection member 35 having a parabolic shape and configured of a material that reflects the electron beam B or the far infrared ray E, it is possible to efficiently heat only the permeable membrane 10.

Figure 7:
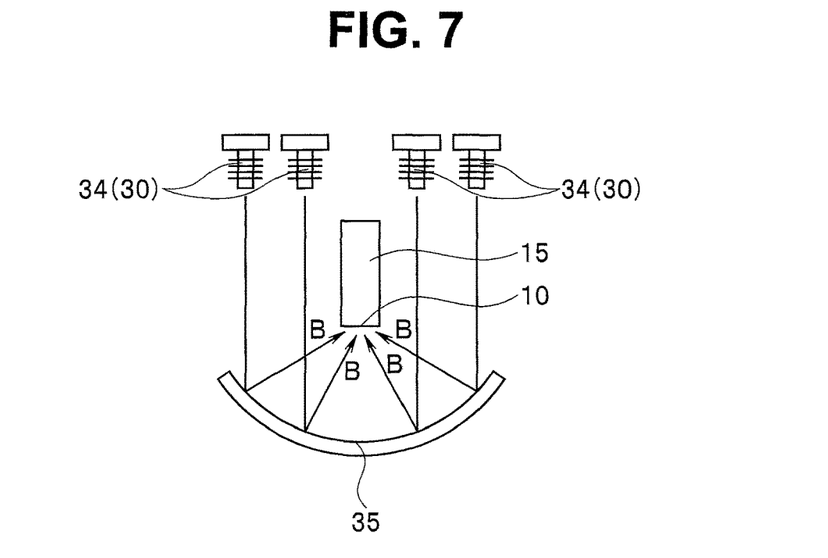
FIG. 7 is a partial sectional view showing, together with a part of the concentration sensor, a state in which an electron beam irradiated from the electron beam irradiator shown in FIG. 6 is intensively irradiated on the permeable membrane by a reflection member.

Note that the configuration shown in FIG. 7 may be used for a configuration for irradiating the far infrared ray E on the permeable membrane 10 from the far infrared ray lamp 33.

Therefore, if the configuration in which the heating section 30 directly heats the permeable membrane 10 is used as shown in FIG. 3 to FIG. 7, as in the present embodiment explained above, it is possible to cause the disinfection solution R to quickly permeate into the permeable membrane 10. Besides, it is possible to minimize the deterioration of the disinfection solution R involved in the heating.

Further, since the permeable membrane 10 can be directly heated, it is possible to reduce the deterioration of the disinfection solution R. Therefore, it is also possible to provide the concentration sensor 15 in the main body section 158. Note that the other effects are the same as the effects explained in the present embodiment.

Second Embodiment

Figure 8:
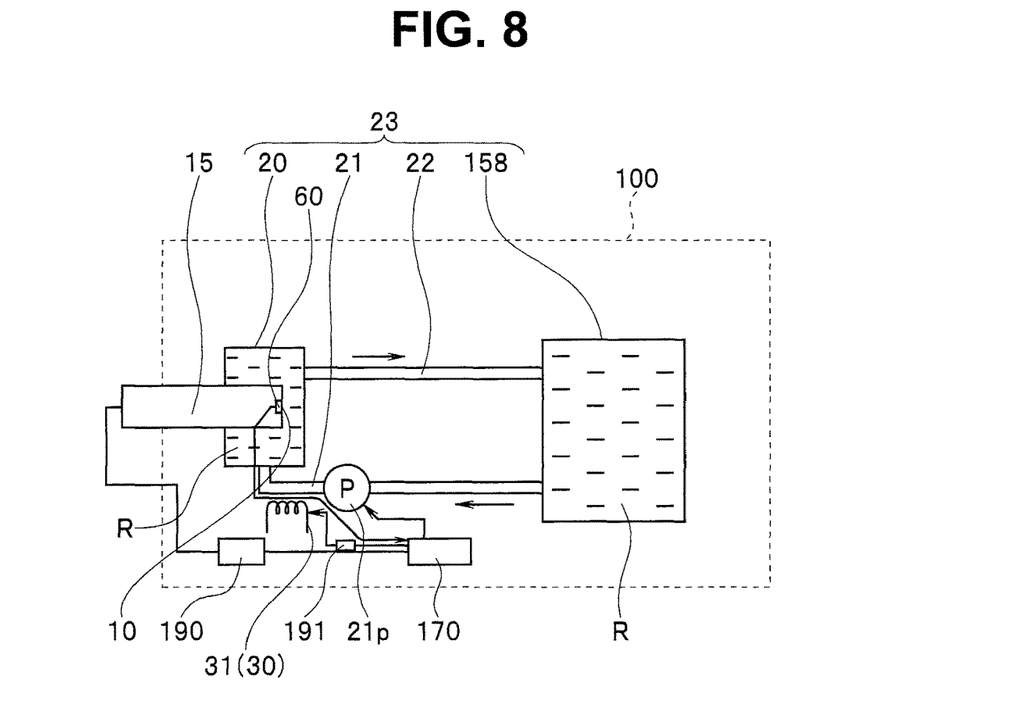
FIG. 8 is a diagram schematically showing a configuration of an endoscope cleaning and disinfecting apparatus of a second embodiment.

FIG. 8 is a diagram schematically showing a configuration of an endoscope cleaning and disinfecting apparatus of a second embodiment.

A configurations of the endoscope cleaning and disinfecting apparatus of the second embodiment is different in that a dryness degree of a permeable membrane is detected and a disinfection solution is heated only when the permeable membrane is dry compared with the configuration of the endoscope cleaning and disinfecting apparatus of the first embodiment shown in FIG. 1 and FIG. 2.

Therefore, the same components as the components in the first embodiment are denoted by the same reference numerals and signs and explanation of the components is omitted.

In the following explanation, a configuration for heating, with the heating section 30, the disinfection solution R supplied to the concentration measurement chamber 20 only in a state in which the permeable membrane 10 does not reach a target humidity as shown in FIG. 15 is explained with reference to FIG. 8.

As shown in FIG. 8, in the present embodiment, in the concentration measurement chamber 20, a dryness detecting section 60 configured to detect a dryness degree of the permeable membrane 10 and electrically connected to the control section 170 is provided.

Note that, in the present embodiment, as the dryness detecting section 60, a hydrometer 59 provided in the permeable membrane 10 is explained as an example.

The control section 170 performs control for driving the heating section 30 via the temperature control section 191 when a dryness degree of the permeable membrane 10 detected by the hydrometer 59 is equal to or larger than a reference value, that is, when it is detected that the permeable membrane 10 is dry.

Note that the reference value of the dryness degree is, for example, a dryness degree in the case in which the permeable membrane 10 is not in contact with the disinfection solution R for several minutes. Note that the other components are the same as the components of the first embodiment explained above.

With such a configuration, when the hydrometer 59 detects that the dryness degree of the permeable membrane 10 is smaller than the reference value, that is, in a state in which the permeable membrane 10 is in contact with the disinfection solution R as shown in FIG. 14 referred to above, since it is unnecessary to heat the disinfection solution R, that is, the permeable membrane 10, the control section 170 does not perform the driving control of the heating section 30.

Subsequently, when the hydrometer 59 detects that the dryness degree of the permeable membrane 10 is equal to or larger than the reference value, that is, in a state in which the permeable membrane 10 is dry as shown in FIG. 15 referred to above, as in the first embodiment, in order to cause the disinfection solution R to quickly permeate into the permeable membrane 10, the control section 170 controls to drive, via the temperature control section 191, the heating section 30 to heat the disinfection solution R.

As a result, the disinfection solution R is heated and the permeable membrane 10 immersed in the disinfection solution R in the concentration measurement chamber 20 is also heated. Therefore, the disinfection solution R is caused to quickly permeate into the permeable membrane 10.

Therefore, it is possible to obtain the same effects as the effects in the first embodiment. Besides, since the permeable membrane 10 is heated using the heating section 30 only when it is detected by the hydrometer 59 that the permeable membrane 10 is dry. Therefore, it is possible to delay thermal deterioration of the disinfection solution R.

Note that, in the present embodiment, as shown in FIG. 3 to FIG. 7, the heating section 30 may directly heat the permeable membrane 10.

Figure 10:
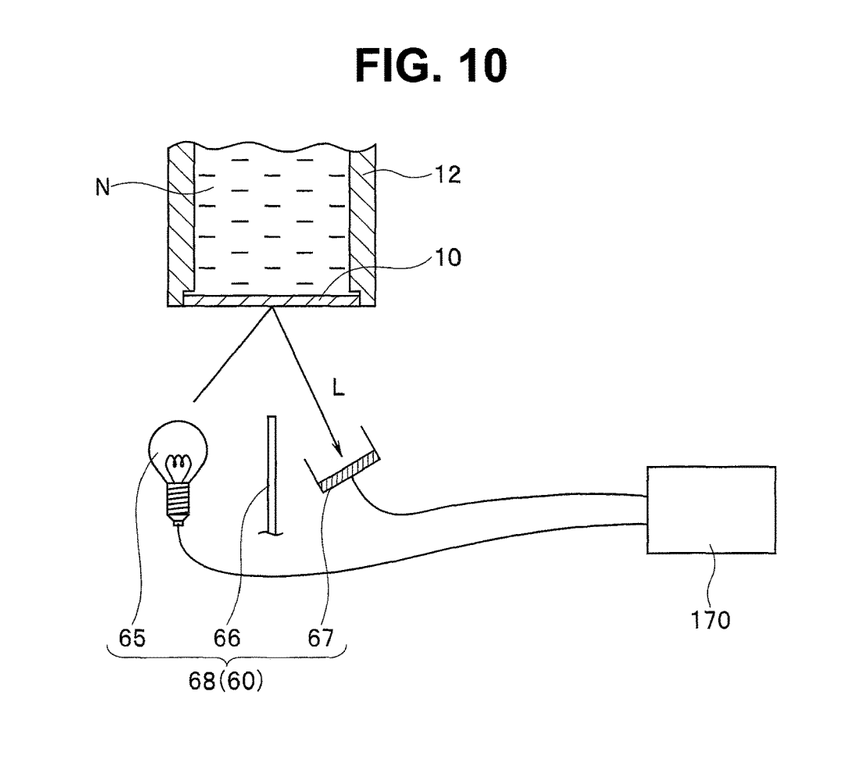
FIG. 10 is a partial sectional view schematically showing a modification in which the dryness detecting section shown in FIG. 8 is configured of a photodetector.
Figure 11:
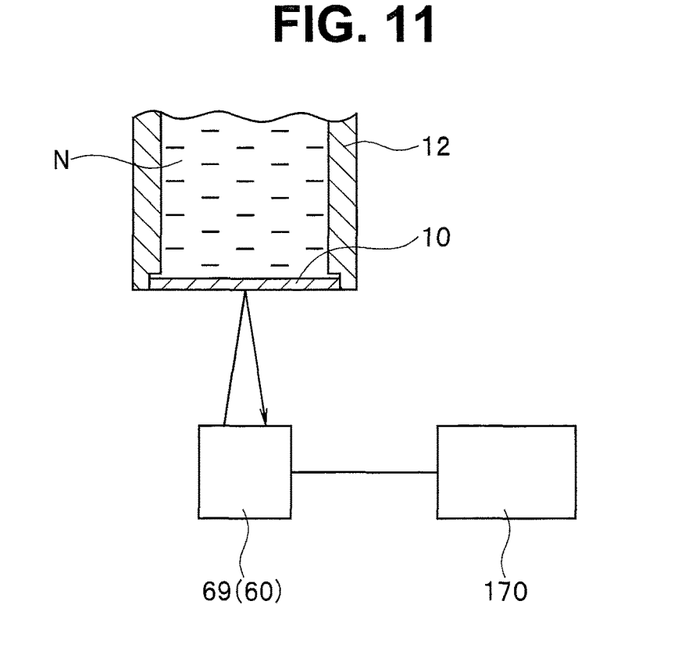
FIG. 11 is a partial sectional view schematically showing a modification in which the dryness detecting section shown in FIG. 8 is configured of a temperature detector.

Further, in the present embodiment explained above, the hydrometer 59 is explained as the example of the dryness detecting section 60. Besides, configurations shown in FIG. 9 to FIG. 11 are conceivable.

Figure 9:
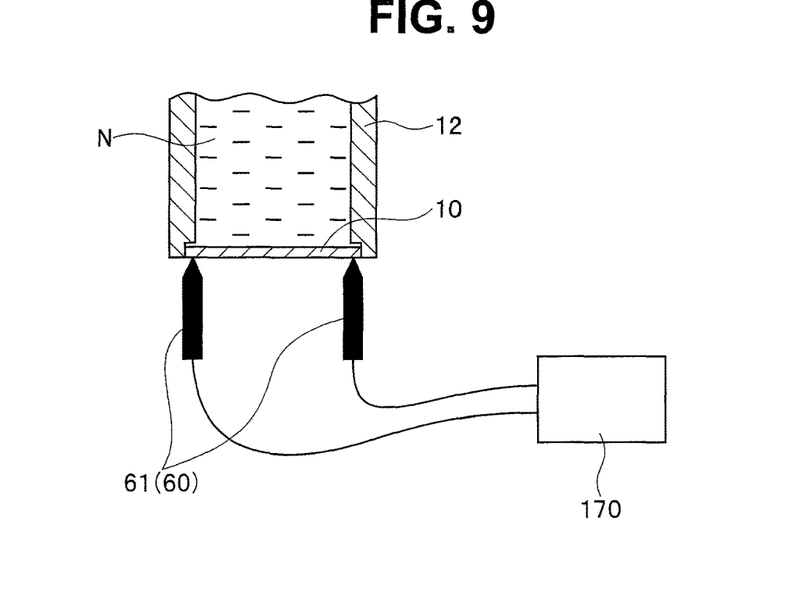
FIG. 9 is a partial sectional view schematically showing a modification in which a dryness detecting section shown in FIG. 8 is configured of an electrode.

FIG. 9 is a partial sectional view schematically showing a modification in which the dryness detecting section shown in FIG. 8 is configured of an electrode.

As shown in FIG. 9, the dryness detecting section 60 may be configured of an electrode 61 electrically connected to the control section 170, in contact with the permeable membrane 10, and configured to energize the permeable membrane 10.

With such a configuration, if resistance of the permeable membrane 10 is measured by energization from the electrode 61, it is possible to detect a dryness degree of the permeable membrane 10.

FIG. 10 is a partial sectional view schematically showing a modification in which the dryness detecting section shown in FIG. 8 is configured of a photodetector.

As shown in FIG. 10, the dryness detecting section 60 may be configured of a photodetector 68 electrically connected to the control section 170.

The photodetector 68 is configured of a light emitting section 65 configured to irradiate light on the permeable membrane 10, a light receiving section 67 configured to receive reflected light from the permeable membrane 10, and a shielding plate 66 configured to shield the light emitting section 65 and the light receiving section 67.

With such a configuration, it is possible to detect a dryness degree of the permeable membrane 10 based on reflectance of light detected by the light receiving section 67.

FIG. 11 is a partial sectional view schematically showing a modification in which the dryness detecting section shown in FIG. 8 is configured of a temperature detector.

As shown in FIG. 11, the dryness detecting section 60 may be configured of a temperature detector 69 electrically connected to the control section 170.

The temperature detector 69 irradiates an infrared ray on the permeable membrane 10 and detects infrared light reflected from the permeable membrane 10.

With such a configuration, when the permeable membrane 10 is wet, temperature is detected low because of evaporation of the disinfection solution R. When the permeable membrane 10 is dry, temperature is detected high. Therefore, it is possible to detect a dryness degree of the permeable membrane 10.

Note that, as other configurations of the dryness detecting section 60, it is conceivable to adopt, for example, a configuration in which a water level gauge is provided in the concentration measurement chamber 20 and it is determined from a water level in the concentration measurement chamber 20 whether the permeable membrane 10 is in contact with the disinfection solution R and a configuration in which a water level in the concentration measurement chamber 20 and a water level in the main body section 158 are set to the same water level and it is determined from a water level gauge provided in the main body section 158 whether the permeable membrane 10 is in contact with the disinfection solution R.

As another method, it is also conceivable to adopt a method of determining according to an elapsed time from a decrease in the water level whether the permeable membrane 10 is in contact with the disinfection solution R.

An example of the configurations of the endoscope cleaning and disinfecting apparatus 100 in the first and second embodiments explained above is explained with reference to FIG. 13.

Figure 13:
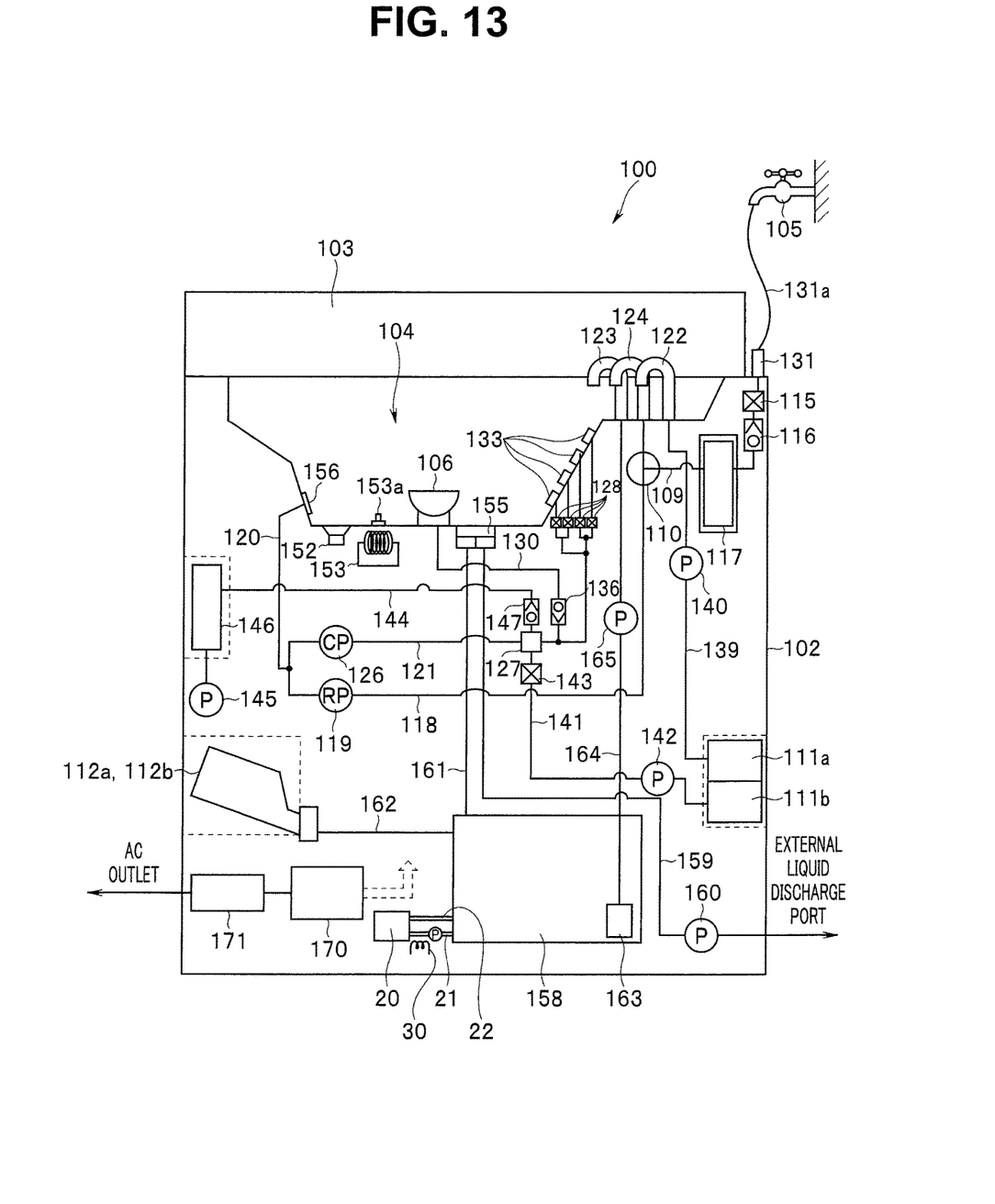
FIG. 13 is a diagram showing an example of an internal configuration of the endoscope cleaning and disinfecting apparatus.

FIG. 13 is a diagram showing an example of an internal configuration of the endoscope cleaning and disinfecting apparatus.

As shown in FIG. 13, the endoscope cleaning and disinfecting apparatus 100 is a device for cleaning and disinfecting a used endoscope. A main part of the endoscope cleaning and disinfecting apparatus 100 is configured of an apparatus main body 102 and a top cover 103 open-closably connected to an upper part of the apparatus main body 102 via, for example, a not-shown hinge.

In the endoscope cleaning and disinfecting apparatus 100, a water-supply-hose connection port 131, to which a faucet 105 is connected via a tube 131a, communicates with one end of a water supply conduit 109. The other end of the water supply conduit 109 is connected to a three-way electromagnetic valve 110. A water-supply electromagnetic valve 115, a check valve 116, and a water supply filter 117 are interposed in order from the water-supply-hose connection port 131 side halfway in the conduit.

Note that the water supply filter 117 is configured as a filtration filter of a cartridge type to be capable of being periodically replaced. The water supply filter 117 removes foreign matter, germs, and the like of tap water passing though the water supply filter 117.

The three-way electromagnetic valve 110 is connected to one end of a liquid flow conduit 118 and switches, with a valve on an inside, communication of the water supply conduit 109 and the liquid flow conduit 118 with a water-supply circulation nozzle 124. That is, the water-supply circulation nozzle 124 communicates with at least one of the water supply conduit 109 and the liquid flow conduit 118 according to a switching operation of the three-way electromagnetic valve 110. A liquid flow pump 119, which is a non-self-priming type pump that can transfer only liquid and is excellent in a transfer ability of liquid, is interposed on the other end side of the liquid flow conduit 118.

A circulation port 156 disposed in a cleaning and disinfecting tub 104 is connected to one end of a circulation conduit 120. The other end of the circulation conduit 120 branches into two to communicate with the other end of the liquid flow conduit 118 and one end of a channel conduit 121. The other end of the channel conduit 121 communicates with respective connectors 133.

In the channel conduit 121, a channel pump 126, a channel block 127, and a channel electromagnetic valve 128 are respectively interposed in order from one end side halfway in the conduit. The other end of a conduit for case 130, one end of which is connected to a cleaning case 106, is connected to the channel conduit 121 between the channel block 127 and the channel electromagnetic valve 128. A relief valve 136 is interposed in the conduit for case 130. Note that the channel pump 126 is configured of a self-priming type pump, which can transfer both of liquid and gas at higher pressure than a non-self-priming type pump.

A detergent nozzle 122 is connected to one end of a cleaning agent conduit 139. The other end of the cleaning agent conduit 139 is connected to a detergent tank 111a. A pump for detergent 140 configured of a high-pressure self-priming type pump for lifting a cleaning agent from the detergent tank 111a to the cleaning and disinfecting tub 104 is interposed halfway in the cleaning agent conduit 139.

An alcohol tank 111b is connected to one end of an alcohol conduit 141. The alcohol conduit 141 is connected to the channel block 127 to communicate with the channel conduit 121 in a predetermined manner.

In the alcohol conduit 141, an alcohol supply pump 142 configured of a high-pressure self-priming type pump for lifting alcohol from the alcohol tank 111b to the cleaning and disinfecting tub 104 and an electromagnetic valve 143 are interposed.

One end of an air conduit 144 for supplying air from an air pump 145 configured of a self-priming type pump, which can transfer gas, is connected to the channel block 127 to communicate with the channel conduit 121 in a predetermined manner. The other end of the air conduit 144 is connected to the air pump 145. A check valve 147 and an air filter 146, which is periodically replaced, are interposed in a halfway position of the air conduit 144.

In a discharge port 155 provided in the cleaning and disinfecting tub 104, a not-shown open-closable valve body for discharging a cleaning solution or the like to an outside and collecting a disinfection solution to the main body section 158 of the medicinal solution tank 23 according to a switching operation of the valve is provided.

The discharge port 155 is connected to the other end of a liquid discharge conduit 159, one end of which is connected to and communicates with a not-shown liquid discharge hose connected to an external liquid discharge port. A water discharge pump 160 configured of a non-self-priming type pump is interposed in the liquid discharge conduit 159. The discharge port 155 is connected to one end of a medicinal solution recovery conduit 161. The other end of the medicinal solution recovery conduit 161 is connected to the main body section 158.

The main body section 158 is connected to one end of a medicinal-solution supply conduit 162 as well such that a disinfection solution is supplied to the main body section 158 from medicinal solution bottles 112a and 112b.

The one end portion of a medicinal solution conduit 164, at one end of which a suction filter 163 is provided, is housed in the main body section 158 in a predetermined manner. The other end of the medicinal solution conduit 164 is connected to a disinfection solution nozzle 123. A high-pressure self-priming type pump 165 for lifting a disinfection solution from the main body section 158 to the cleaning and disinfecting tub 104 is interposed in a halfway position of the medicinal solution conduit 164.

Further, as explained above, the concentration measurement chamber 20 is connected to the main body section 158 via the medicinal-solution lead-in section 21 and the medicinal-solution lead-out section 22.

Note that, for example, two vibrating sections 152 and a heater 153 are disposed in a lower part of a bottom surface of the cleaning and disinfecting tub 104. For temperature adjustment of the heater 153, a temperature detection sensor 153a is provided substantially in a center of the bottom surface of the cleaning and disinfecting tub 104.

A power supply 171, to which electric power is supplied from an external AC receptacle, and a control section 170 electrically connected to the power supply 171 are provided on an inside of the endoscope cleaning and disinfecting apparatus 100.

Third Embodiment

Figure 12:
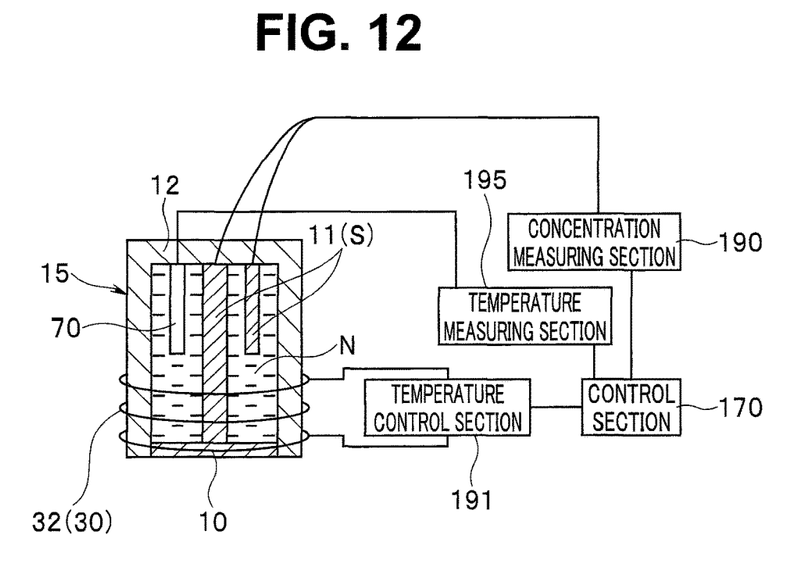
FIG. 12 is a diagram schematically showing a configuration of an endoscope cleaning and disinfecting apparatus of a third embodiment.

FIG. 12 is different from the first and second embodiments in that an endoscope cleaning and disinfecting apparatus includes a thermometer 70 and a temperature measuring section 195 configured to measure temperature of the internal solution N and in that the control section 170 controls the heating section 30 on the basis of the temperature of the internal solution N.

In FIG. 12, the heating section 30 configured to heat the internal solution N is shown. However, the endoscope cleaning and disinfecting apparatus may include a cooling section configured to cool the internal solution N. As an example of the cooling section, there is a Peltier element, an air cooled tube, or a water cooled tube.

It is possible to stabilize accuracy of concentration measurement by adjusting, with the heating section 30 or the heating section and the cooling section, the temperature of the internal solution N to be within a predetermined range.

The temperature control for the internal solution N is not limitedly performed when the permeable membrane 10 is in a dry state and can also be performed when the permeable membrane 10 is in an infiltration state.

In FIG. 12, the electric heating wire 32 disposed on an outer circumference of a concave section is shown as an example of the heating section 30. However, independently of this, it is also possible to adopt, for example, the structures explained in the first embodiment and the modifications.

It is also possible to adopt a structure in which the heating section is immersed in the internal solution or a structure in which the heating section is embedded in the concave section.

Note that the configuration of the endoscope cleaning and disinfecting apparatus explained above with reference to FIG. 14 is only an example and is not limited to this configuration. The endoscope reprocessor is not limited to the endoscope cleaning and disinfecting apparatus and is also applicable to a sterilization apparatus and the like in which a medicinal solution is used.

Further, the present embodiment is also applicable to detection of components other than the disinfection solution. The present embodiment is not limited to the detection of the peracetic acid concentration in the medicinal solution and is also applicable to oxygen concentration detection in the medicinal solution, detection of a pH value, and the like.

In the first and second embodiments explained above, in the concentration sensor 15, the internal solution N is sealed in the concave section 12 by the permeable membrane 10. The electrode 11 is explained as the example of the sensing section S provided in the concave section 12. However, independently of this, the first and second embodiments are applicable if the internal solution N is not provided in the concave section 12 and, for example, a gas detection sensor is used as the sensing section S.

When the gas detection sensor is used as the sensing section, it is desirable that air not including a measurement target component or relatively stable nitrogen or rare gas is filled in the concave section 12 instead of the internal solution N.

What is claimed is:

1. An endoscope reprocessor comprising:
    a concave housing;
    a concentration sensor disposed in the concave housing, the concentration sensor being configured to detect a fluid concentration in the concave housing;
    a permeable membrane configured to cover the concave housing;
    a medicinal solution tank, at least the permeable membrane being exposed to an inside of the medicinal solution tank and a medicinal solution being stored in the inside of the medicinal solution tank; and
    a heater configured to heat at least the permeable membrane.

2. The endoscope reprocessor according to claim 1, further comprising:
    an internal solution sealed in the concave housing by the permeable membrane, and
    the concentration sensor includes an electrode, at least a part of the electrode being immersed in the internal solution.

3. The endoscope reprocessor according to claim 1, wherein the medicinal solution tank includes:
    a main body in which the medicinal solution is stored;
    a concentration measurement chamber, a capacity of the concentration measurement chamber being smaller than a capacity of the main body, the concentration sensor being disposed on an inside of the concentration measurement chamber to expose at least the permeable membrane; and
    a medicinal-solution lead-in conduit configured to introduce the medicinal solution into the concentration measurement chamber from the main body.

4. The endoscope reprocessor according to claim 3, wherein
    the medicinal solution tank further includes a medicinal-solution lead-out conduit configured to introduce the medicinal solution into the main body from the concentration measurement chamber,
    the medicinal-solution lead-in conduit includes a medicinal-solution pump configured to transfer the medicinal solution in the main body, and
    the medicinal solution is circulated between the main body and the concentration measurement chamber via the medicinal-solution lead-in conduit and the medicinal-solution lead-out conduit according to driving of the medicinal-solution pump.

5. The endoscope reprocessor according to claim 3, wherein, in the medicinal-solution lead-in conduit or in the concentration measurement chamber, the heater is configured to further heat the medicinal solution to thereby heat the permeable membrane via the medicinal solution and heats the medicinal solution to a temperature higher than a service temperature of the medicinal solution.

6. The endoscope reprocessor according to claim 1, wherein the heater is configured to directly heat the permeable membrane in the medicinal solution tank.

7. The endoscope reprocessor according to claim 1, further comprising:
    a dryness detecting sensor configured to detect a dryness degree of the permeable membrane; and
    a controller comprising hardware, the controller being connected to the heater and to the dryness detecting sensor, wherein
    the controller is configured to control driving of the heater when the dryness degree of the permeable membrane detected by the dryness detecting sensor is equal to or larger than a reference value.

* * * * *